(12) United States Patent  (10) Patent No.: US 8,287,202 B2
Goodman et al.  (45) Date of Patent: Oct. 16, 2012

(54) METHOD FOR DISPENSING A POLYMERIZABLE MONOMER ADHESIVE

(75) Inventors: Jack Goodman, Ann Arbor, MI (US); Gregory Hake, Otsego, MN (US); Thomas Schoon, Shoreview, MN (US); Thomas A Shepard, Rolesville, NC (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 13/345,468

(22) Filed: Jan. 6, 2012

(65) Prior Publication Data

US 2012/0160867 A1 Jun. 28, 2012

Related U.S. Application Data

(62) Division of application No. 11/565,022, filed on Nov. 30, 2006, now Pat. No. 8,118,508.

(51) Int. Cl.
*B43K 5/14* (2006.01)
(52) U.S. Cl. ............................. 401/133; 401/132; 604/3
(58) Field of Classification Search .......... 401/132–135; 604/3
See application file for complete search history.

(56) References Cited

U.S. PATENT DOCUMENTS

| | | | |
|---|---|---|---|
| 2,721,858 A | 10/1955 | Joyner et al. | |
| 3,254,111 A | 5/1966 | Hawkins et al. | |
| 3,554,990 A | 1/1971 | Quinn et al. | |
| 3,940,362 A | 2/1976 | Overhults | |
| 3,995,641 A | 12/1976 | Kronenthal et al. | |
| 4,313,865 A | 2/1982 | Teramoto et al. | |
| 4,364,876 A | 12/1982 | Kimura et al. | |
| 4,560,723 A | 12/1985 | Millet et al. | |
| 4,720,513 A | 1/1988 | Kameyama et al. | |
| 4,784,506 A | 11/1988 | Koreska et al. | |
| 4,793,887 A | 12/1988 | Card et al. | |
| 4,793,888 A | 12/1988 | Card et al. | |
| 5,328,687 A | 7/1994 | Leung et al. | |
| 5,358,349 A | 10/1994 | Burroughs et al. | |
| 5,568,988 A | 10/1996 | Knox et al. | |
| 5,702,759 A | 12/1997 | White et al. | |
| 5,924,206 A | 7/1999 | Cote et al. | |

(Continued)

FOREIGN PATENT DOCUMENTS

GB 2078763 A 1/1982

OTHER PUBLICATIONS

International Search Report Completed May 14, 2008 in corresponding International Patent Application No. PCT/US2007/085236, filed Nov. 20, 2007.

*Primary Examiner* — David Walczak

(57) ABSTRACT

This invention generally relates to a method of dispensing an adhesive material using an applicator comprising: a body having a cavity; at least one breaking member integral with the body and having a surrounding gap, the breaking member deflectable into the cavity and having a first engagement member; an annular housing movable with respect to the body and having a second engagement member complementary with the first engagement member, the first and the second engagement members being cooperatively engageable; a reservoir secured to body and having applicator means; a retaining member between the body and reservoir; and a frangible container of adhesive material disposed within the cavity; moving the annular housing relative to the body from a first position to a second position where the engagement members are cooperatively engaged; deflecting the breaking members and breaking the frangible container; and squeezing the reservoir and dispensing adhesive material.

4 Claims, 9 Drawing Sheets

U.S. PATENT DOCUMENTS

| | | |
|---|---|---|
| 5,928,611 A | 7/1999 | Leung |
| 6,010,263 A | 1/2000 | White et al. |
| 6,048,921 A | 4/2000 | White et al. |
| 6,062,753 A | 5/2000 | Hadtke et al. |
| 6,143,352 A | 11/2000 | Clark et al. |
| 6,143,805 A | 11/2000 | Hickey et al. |
| 6,155,265 A | 12/2000 | Hammerslag |
| 6,183,593 B1 | 2/2001 | Narang et al. |
| 6,310,166 B1 | 10/2001 | Hickey et al. |
| 6,341,912 B1 | 1/2002 | Gueret |
| 6,386,203 B1 | 5/2002 | Hammerslag |
| 6,425,704 B2 | 7/2002 | Voiers et al. |
| D465,279 S | 11/2002 | Etter et al. |
| D469,694 S | 2/2003 | Lerolle |
| D472,578 S | 4/2003 | Plantz et al. |
| 6,579,469 B1 | 6/2003 | Nicholson et al. |
| 6,582,453 B1 | 6/2003 | Tran et al. |
| 6,620,846 B1 | 9/2003 | Jonn et al. |
| 6,673,192 B1 | 1/2004 | Woods et al. |
| 6,705,790 B2 | 3/2004 | Quintero et al. |
| 6,755,585 B2 | 6/2004 | Gueret |
| D493,484 S | 7/2004 | Shova et al. |
| D494,270 S | 8/2004 | Reschke |
| 6,783,035 B2 | 8/2004 | Garcia et al. |
| D500,085 S | 12/2004 | Cotter et al. |
| D502,739 S | 3/2005 | Shova et al. |
| D521,385 S | 5/2006 | Priestman |
| 7,182,536 B2 * | 2/2007 | Tufts et al. ............ 401/133 |
| D537,710 S | 3/2007 | Blasko et al. |
| D539,420 S | 3/2007 | Zahn et al. |
| 7,306,390 B2 | 12/2007 | Quintero et al. |
| D559,385 S | 1/2008 | Boone et al. |
| 7,371,345 B2 | 5/2008 | Stewart et al. |
| D571,010 S | 6/2008 | Cote |
| 7,422,388 B2 * | 9/2008 | Tufts et al. ............ 401/133 |
| 7,516,872 B2 | 4/2009 | Boone et al. |
| 2002/0037310 A1 | 3/2002 | Jonn et al. |
| 2005/0182443 A1 | 8/2005 | Jonn et al. |
| 2006/0009099 A1 | 1/2006 | Jonn et al. |
| 2006/0049203 A1 | 3/2006 | Boone et al. |
| 2008/0131190 A1 | 6/2008 | Goodman et al. |

* cited by examiner

METHOD FOR DISPENSING A POLYMERIZABLE MONOMER ADHESIVE

CROSS REFERENCE TO RELATED APPLICATIONS

This divisional application claims the benefit of parent application Ser. No. 11/565,022, filed Nov. 30, 2006, which is published as US 2008/0131190 A1, now U.S. Pat. No. 8,118,508.

FIELD

The present invention relates to a dispenser such as an adhesive applicator device, in particular, an adhesive applicator device for applying/dispensing a polymerizable adhesive composition.

BACKGROUND

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal (including human) tissue. Monomers of α-cyanoacrylates are anionically polymerizable or free radical polymerizable, or polymerizable by zwitterions or ion pairs to form polymers. Once polymerization has been initiated, the cure rate may be very rapid.

Medical applications of 1,1-disubstituted ethylene adhesive compositions include use as an alternate or an adjunct to surgical sutures and/or staples in wound closure, as well as for covering and protecting surface wounds such as lacerations, abrasions, burns, stomatitis, sores, minor cuts and scrapes, and other wounds. When an adhesive is applied to surfaces to be joined, it is usually applied in its monomeric form, and the resultant polymerization gives rise to the desired adhesive bond.

However, due to the need to apply the adhesive or sealant material in its monomeric form, and due to the rapid polymerization rate of the monomers, it has been very difficult to design effective and commercially viable applicators and/or dispensers. Such applicators and/or dispensers must balance the competing requirements that the monomer not prematurely polymerize, that the monomer be easily applied, that the monomer polymerize at a desired rate upon application, and that the sanitary and/or sterile properties of the monomer and applicator be maintained.

Problems with known applicators and/or dispensers include, for example, the adhesive or sealant material being fed from the applicator device by gravity only. Such gravity feed methods may not allow for desired control over the flow of the adhesive or sealant material from the applicator device during use. Furthermore, known applicators/dispensers may not allow for fine control over and placement of the adhesive or sealant material at the time of use.

SUMMARY

The above needs are addressed by providing applicators and dispensers that permit economical and efficient use of adhesive or sealant compositions. In embodiments applicators and/or dispensers are provided that are user friendly.

In one embodiment, an applicator device for dispensing a polymerizable adhesive material is provided. The applicator device comprises a body portion comprising a closed proximal end and an open distal end providing a cavity. The cavity is sized to accept a frangible container having a polymerizable adhesive material. At least one breaking member is integral with the body portion and each breaking member has a surrounding gap. The at least one breaking member is at least partially deflectable into the cavity and each breaking member has a first engagement member. An annular housing is movable with respect to the body portion and has a second engagement member complementary with the at least one first engagement member, the first and the second engagement member being cooperatively engageable with each other. A reservoir is secured to the open distal end of the body portion, the reservoir having applicator means. A retaining member is located between the body portion and the reservoir. When the annular housing is moved relative to the body portion from a first position where the first and the second engagement members are not cooperatively engaged with each other, to a second position where the first and the second engagement members are cooperatively engaged with each other, at least a portion of the breaking member is deflected into the cavity, breaking or piercing the frangible container and allowing adhesive material to flow into the reservoir.

In another embodiment, an applicator device for dispensing a polymerizable adhesive material is provided. The applicator device comprises a body portion comprising a closed proximal end and an open distal end providing a cavity. A plurality of breaking members are integral with the body portion and each breaking member has a surrounding gap, the plurality of breaking members are at least partially deflectable into the cavity and each breaking member has a first engagement member. At least one semi-rigid section sealably contacts each of the plurality of breaking members and sealably covers each corresponding surrounding gap. An annular housing is circumferentially rotatable with respect to the body portion and has a second engagement member complementary with the first engagement member, the first and the second engagement member being cooperatively engageable with each other. A reservoir is secured to the open distal end of the body portion. The reservoir has a distal opening which comprises applicator means. A retaining member is located between the body portion and the reservoir. A flow restrictor is proximal to the distal opening of the reservoir. A frangible container of polymerizable monomer adhesive material is disposed within the cavity between the closed proximal end and the retaining member. When the annular housing is circumferentially rotated relative to the body portion from a first position where the first and the second engagement member are not cooperatively engaged with each other, to a second position where the first and the second engagement member are cooperatively engaged with each other, at least a portion of the breaking member is deflected into the cavity, breaking or piercing the frangible container and allowing adhesive material to flow into the reservoir.

In another embodiment, a method of applying/dispensing an adhesive material is provided. The method comprises providing an applicator device for dispensing and/or applying an adhesive material. The applicator device comprises a body portion comprising a closed proximal end and an open distal end providing a cavity. At least one breaking member is integral with the body portion, each breaking member having a surrounding gap, and the at least one breaking member is at least partially deflectable into the cavity. Each breaking member has a first engagement member. An annular housing is movable with respect to the body portion and has a second engagement member complementary with the first engagement member, the first and the second engagement member being cooperatively engageable with each other. A reservoir is secured to the open distal end of the body portion, the reservoir further having a distal opening comprising applicator means. A retaining member is located between the body portion and the reservoir and a frangible container of adhesive material is disposed within the cavity between the closed proximal end and the retaining member. Moving the annular housing relative to the body portion from a first position, where the first and the second engagement members are not cooperatively engaged with each other, to a second position where the first and the second engagement members are cooperatively engaged with each other, deflects at least a portion of the breaking member into the cavity breaking or piercing the frangible container. Squeezing the reservoir provides a positive pressure within the reservoir, dispensing adhesive material from the reservoir to a substrate. Releasing the squeezed reservoir creates a negative pressure within the reservoir for urging adhesive material from the container within the cavity into the reservoir.

DETAILED DESCRIPTION

Figure 1:
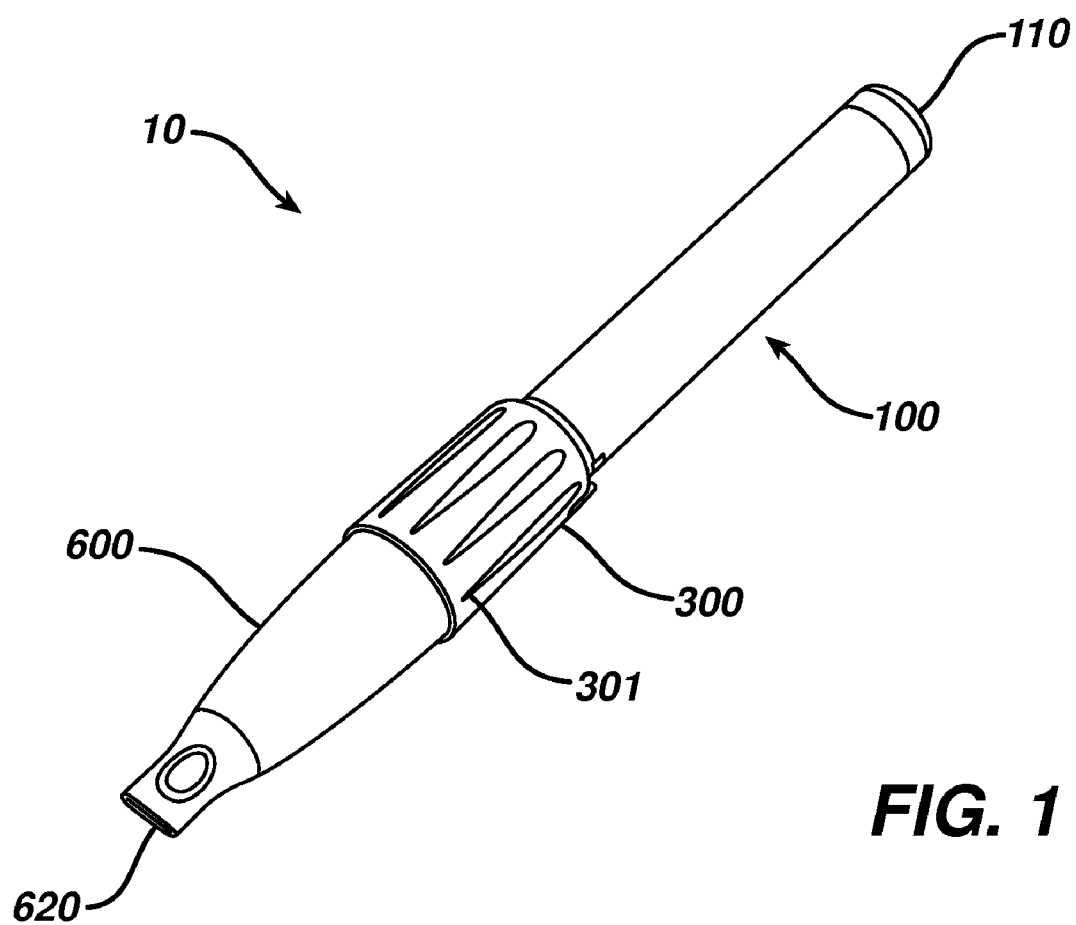
FIG. 1 illustrates a top perspective view of an applicator device embodiment.

In embodiments, an applicator and/or dispenser (herein after referred to as "applicator device") is designed to facilitate manipulation by hand for mixing, dispensing and/or applying an adhesive or sealant material. For example, applicators and/or dispensers are provided that are pen-like, providing a familiar feel to the user. In embodiments, an applicator is designed to reduce or eliminate leakage of adhesive from the device, be more securably gripped by the user, be more comfortable to the user, and/or easier to operate. The applicator allows for a "hands forward" position on the applicator device providing greater control over placement of the adhesive or sealant material. Additionally, the placement and length of the actuator allows for ease of use of the applicator while maintaining the hands forward position thereby allowing for greater control over the flow and direction of the adhesive or sealant material. In embodiments, the actuator may be recessed into the body portion such that it is flush to the body of the applicator.

In particular, embodiments are directed to an applicator device for dispensing, mixing and/or applying an adhesive or sealant material, comprising: a body portion; a cavity in the body portion; an actuator movable relative to the body portion; and at least one breaking member integral with the body portion and cooperatively engageable by the actuator, wherein movement of the actuator relative to the body portion moves at least a portion of at least one breaking member into the cavity of the body portion.

In embodiments, the applicator device comprises a body portion. The body portion includes a closed proximal end and an open distal end which forms a cavity within the body portion. The cavity may be sized to accept a frangible container of adhesive or sealant material. The body portion may comprise one or more body segments. The closed distal end may comprise re-sealable means such as a screw cap or snap-fit cap for insertion of a frangible container at the point of use. The screw cap or snap-fit cap preferably is designed to lock upon sealing with the body to prevent re-opening. The body portion or a body segment of the body portion may be molded or machined.

In various embodiments, the applicator device further comprises a frangible container of adhesive or sealant material at least partially disposed within the cavity, wherein movement of the actuator relative to the body portion moves the breaking member(s) to rupture the frangible container.

In embodiments, the body portion or a body segment of the body portion comprises at least one breaking member. The breaking member is formed from one or more surrounding gaps in the body portion. The breaking member may be proximally integral with the body portion and distally extend in a generally parallel direction with the longitudinal axis of the body portion. Alternatively, the breaking member may be distally integral with the body portion and proximally extend in a generally parallel direction with the longitudinal axis of the body portion. The breaking member may be circumferentially integral with the body portion. The breaking member is deflectable such that at least a portion of the breaking member enters the cavity. There may be only one breaking member or there may be a plurality of breaking members. The term "plurality" as used herein refers to at least two. In embodiments, there are two breaking members. The breaking members comprise a first engagement member near or at their distal end. The first engagement member may be a lobe, tine, protrusion, or equivalent. The first engagement member may alternatively be a recess, cam race or equivalent. The breaking member(s) may be positioned anywhere on the body portion or a body segment of the body portion such that upon deflection at least a portion of the breaking member(s) enters the cavity.

In embodiments, the applicator device comprises at least one semi-rigid section. The semi-rigid section provides a seal such that adhesive material is restricted from leaking from the body portion of the applicator device. The semi-rigid section sealably contacts each of the at least one breaking member and sealably covers each corresponding surrounding gap. There may be a plurality of breaking members and corresponding gaps that are contacted and sealed by a single semi-rigid section. Alternatively, each breaking member and corresponding gap may be contacted and sealed by a separate semi-rigid section. The semi-rigid portion provides a seal about the breaking member and the corresponding gap in the body portion reducing or eliminating leakage from the cavity after the frangible container has been ruptured. In embodiments, the semi-rigid portion sealably contacts the breaking members by essentially overlaying the breaking member with the exception of at least a portion of the engagement member of the breaking member. This may be achieved by providing an orifice such as a hole in the semi-rigid section for outward protrusion of the engagement member of the breaking member. The semi-rigid portion is generally of a material less rigid than the body portion. The semi-rigid portion may be a thermoplastic elastomer. The semi-rigid section may be formed by co-injection molding, insert molding or overmolding. In embodiments, the semi-rigid section may be formed out of the body portion or a body segment of the body portion, for example, as a thin-walled section.

In embodiments, the applicator device comprises an actuator. In embodiments, the actuator comprises a movable annular housing or annular collar. The terms "annular housing" and "annular collar" are used herein interchangeably. The annular housing may contain a second engagement member. The second engagement member of the movable annular housing engages at least one first engagement member of the breaking member. The second engagement member is complementary with the first engagement member. For example, when the first engagement member is a lobe, tine, protrusion, or equivalent, the second engagement member may be a cam, cam race or equivalent, or a thickened wall section. Alternatively, if the first engagement member is a cam, cam race or equivalent or thickened wall section, the second engagement member may be a lobe, tine, protrusion, or equivalent.

In embodiments, the actuator comprises an annular housing movably mounted on the body portion. The annular housing may be circumferentially rotatable or axially movably mounted on the body portion from a first position where the first and the second engagement member are not cooperatively engaged with each other, to a second position where the first and the second engagement member are cooperatively engaged with each other such that the breaking member is deflected into the cavity when the annular housing is in the second position. In embodiments, the annular housing is rotatable circumferentially relative to the body portion from a first position where the first and the second engagement member are not cooperatively engaged with each other, to a second position where the first and the second engagement member are cooperatively engaged with each other such that the breaking member is deflected into the cavity when the annular housing is in the second position. In embodiments, the annular housing is axially movable relative to the body portion from a first position where the first and the second engagement member are not cooperatively engaged with each other, to a second position where the first and the second engagement member are cooperatively engaged with each other such that the breaking member is deflected into the cavity when the annular housing is in the second position. In embodiments, the annular housing is circumferentially rotatable and non-axially movable relative to the body portion from a first position where the first and the second engagement member are not cooperatively engaged with each other, to a second position where the first and the second engagement member are cooperatively engaged with each other such that the breaking member is deflected into the cavity when the annular housing is in the second position. By way of example, upon movement of the annular housing from the first position to the second position, the first and the second engagement member are cooperatively engaged with each other such that at least a portion of at least one breaking member is deflected into the cavity to rupture the frangible container. In embodiments, movement of the actuator relative to the body portion to move at least a portion of the breaking member into the cavity is inhibited prior to use of the applicator device.

In embodiments, the applicator device further comprises a retaining member at least partially disposed in the open distal end of the body portion. The retaining member may be positioned between the body portion and a reservoir. The retaining member directs flow of the polymerizable adhesive material from the body portion into the reservoir and/or provides for venting. The retaining member restrains fragments of broken frangible container within the body portion. The retaining member is preferably positioned proximal to the distal opening of the reservoir. The retaining member may be made of a material that is at least one of porous, absorbent and adsorbent in nature. The retaining member may be made of a wicking material. The retaining member may comprise a one-way flow controlling element in combination with a venting element such that air may easily or unimpededly enter the cavity as adhesive or sealant material concurrently leaves the cavity. In embodiments, the retaining element may comprise a plurality of orifices. For example, the retaining element may comprise a generally centered orifice circumferentially surrounded by generally smaller orifices such that air may easily or unimpededly enter the cavity as adhesive or sealant material concurrently leaves the cavity.

In embodiments, the retaining member may further comprise a filter to prevent particles of the broken frangible container from exiting the cavity. The filter may be positioned between the retaining member and the frangible container. Alternatively, the filter may be positioned such that the retaining member is between the filter and the frangible container. The filter may be integral with the retaining member. The filter may be any material or may be compatible or non-interactive with the polymerizable adhesive material. By way of example, the filter may be a screen or porous disk. By further way of example, the filter may be of polyethylene (e.g., high-density or ultra-high molecular weight), polyethylene terephthalate (PET), polypropylene, glass or metal etched with holes. In embodiments, at least one of a medicament, a polymerization initiator, a polymerization rate modifier and a stabilizer for a polymerizable monomer is in or on the retaining member and/or in or on the filter.

In embodiments, the applicator device further comprises a reservoir secured to the open distal end of the body portion. The reservoir is in fluid communication with the cavity to receive the adhesive or sealant material. The reservoir is essentially a hollow chamber which may function as a reservoir, siphon and/or dispensing pump. The reservoir may siphon adhesive from the cavity when released after squeezing because of a differential pressure that is caused by the recovery of the reservoir to its original shape. The reservoir may be flexible, semi-flexible, semi-rigid, reinforced or an exoskeleton. In embodiments, the reservoir is flexible. The reservoir may be of any material which is compatible with the adhesive or sealant material such as polysilicones, KRATON®, polyurethanes, thermoplastic elastomer, and the like. In embodiments, at least one of a medicament, a polymerization initiator, a polymerization rate modifier and a stabilizer for a polymerizable monomer is in or on the reservoir. The reservoir may be molded, for example, by liquid injection molding (LIM).

In embodiments, the applicator device further comprises applicator means such as an applicator device tip that is connected to or integral with the reservoir. In embodiments, the applicator means may comprise one of a tube, a nozzle, a spatula, a rolling ball, a brush, and a swab. In embodiments, the applicator means such as an applicator device tip is removable and/or interchangeable. Examples of tips for applicators may be found in U.S. Pat. Nos. 6,425,704 and 6,705,790, incorporated herein by reference in their entireties.

In embodiments, the applicator device further comprises a flow restrictor disposed in the reservoir proximal to the applicator device tip, the flow restrictor providing a restricted flow of a material when the material is being dispensed from the reservoir. The flow restrictor may be frictionally secured proximal to the applicator device tip. The flow restrictor may be a machined plug, which may contain an orifice. The flow restrictor preferably restricts flow more than the retaining member and/or filter fluid path from the body portion to the reservoir. In embodiments, at least one of a medicament, a polymerization initiator, a polymerization rate modifier and a stabilizer for a polymerizable monomer is in or on the flow restrictor. In embodiments, at least one of a medicament, a polymerization initiator, a polymerization rate modifier and a stabilizer for a polymerizable monomer is in or on the retaining member/filter, in or on the reservoir, in or on the flow restrictor, and/or in or on the applicator means.

In other embodiments, a method of applying/dispensing an adhesive or sealant material is provided. The method comprises providing an applicator device including a container of adhesive or sealant material at least partially in the cavity of the applicator device; moving an actuator relative to the body portion to deflect a breaking member to rupture the container; squeezing a flexible reservoir to siphon the adhesive from the cavity; and dispensing the adhesive or sealant material from the reservoir. In embodiments, the method further comprises applying the dispensed adhesive or sealant material to a substrate to be bonded. The substrate may be any material requiring adhesive or sealant, including living tissue, particularly in medical embodiments. The substrate may be a flexible material such as a mesh. In embodiments, the mesh comprises at least one of a medicament, a polymerization initiator, a polymerization rate modifier and/or a stabilizer for a polymerizable monomer and/or an adhesive material.

In other embodiments, the method comprises placing a container of adhesive or sealant material at least partially into the cavity of an applicator device; moving the actuator relative to the body portion to deflect the breaking member to rupture the container; squeezing the flexible reservoir to siphon the adhesive from the cavity and dispensing the adhesive or sealant material from the reservoir.

In embodiments, the applicator device comprises a frangible container that includes one or more adhesive, or sealant materials. As used herein, the terms "ampoule" and "cartridge" are used interchangeably and refer to a frangible container capable of containing an adhesive or adhesive composition or sealant material. The term "frangible" in the context of a container refers generally to the ability of the container to be readily or easily broken or ruptured such that the contents of the container are released. The adhesive or sealant material may comprise a polymerizable monomeric adhesive or sealant material. In embodiments, the adhesive or sealant material comprises a polymerizable 1,1-disubstituted ethylene monomer formulation. In embodiments, the adhesive or sealant material comprises a cyanoacrylate formulation. In embodiments, synthetic adhesive materials such as polyurethane, polyethylene glycol, acrylates, glutaraldehyde and biologically based adhesives may be used.

Monomers that may be used in the frangible container of the applicator/dispenser are readily polymerizable, e.g. anionically polymerizable or free radical polymerizable, or polymerizable by zwitterions or ion pairs to form polymers. Some such monomers are disclosed in, for example, U.S. Pat. No. 5,328,687 to Leung, et al., which is hereby incorporated by reference in its entirety herein. Preferably, the cyanoacrylate adhesive compositions comprise one or more polymerizable cyanoacrylate monomers and are biocompatible. The term "biocompatible" refers to a material being suited for and meeting the requirements of a medical device, used for either long or short term implants or for non-implantable applications, such that when implanted or applied in an intended location, the material serves the intended function for the required amount of time without causing an unacceptable response. Long term implants are defined as items implanted for more than 30 days.

The cyanoacrylate adhesive compositions comprising one or more polymerizable cyanoacrylate monomers may include combinations or mixtures of cyanoacrylate monomers.

By way of example, useful monomers include α-cyanoacrylates of formula (I). These monomers are known in the art and have the formula

(I)

wherein $R^2$ is hydrogen and $R^3$ is a hydrocarbyl or substituted hydrocarbyl group; a group having the formula —$R^4$—O—$R^5$—O—$R^6$, wherein $R^4$ is a 1,2-alkylene group having 2-4 carbon atoms, $R^5$ is an alkylene group having 1-4 carbon atoms, and $R^6$ is an alkyl group having 1-6 carbon atoms; or a group having the formula

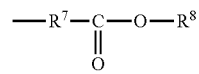

wherein $R^7$ is

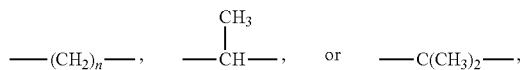

wherein n is 1-10, preferably 1-5 carbon atoms, and $R^8$ is an organic moiety.

Examples of suitable hydrocarbyl and substituted hydrocarbyl groups include straight chain or branched chain alkyl groups having 1-16 carbon atoms; straight chain or branched chain $C_1$-$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety $R^8$ may be substituted or unsubstituted and may be straight chain, branched or cyclic, saturated, unsaturated or aromatic. Examples of such organic moieties include $C_1$-$C_8$ alkyl moieties, $C_2$-$C_8$ alkenyl moieties, $C_2$-$C_8$ alkynyl moieties, $C_3$-$C_{12}$ cycloaliphatic moieties, aryl moieties such as phenyl and substituted phenyl and aralkyl moieties such as benzyl, methylbenzyl, and phenylethyl. Other organic moieties include substituted hydrocarbon moieties, such as halo (e.g., chloro-, fluoro- and bromo-substituted hydrocarbons) and oxy-substituted hydrocarbon (e.g., alkoxy substituted hydrocarbons) moieties. Preferred organic radicals are alkyl, alkenyl, and alkynyl moieties having from 1 to about 8 carbon atoms, and halo-substituted derivatives thereof. Particularly preferred are alkyl moieties of 4 to 6 carbon atoms.

In the cyanoacrylate monomer of formula (I), $R^3$ may be an alkyl group having 1-10 carbon atoms or a group having the formula -$AOR^9$, wherein A is a divalent straight or branched chain alkylene or oxyalkylene moiety having 2-8 carbon atoms, and $R^9$ is a straight or branched alkyl moiety having 1-8 carbon atoms.

Examples of groups represented by the formula -$AOR^9$ include 1-methoxy-2-propyl, 2-butoxy ethyl, isopropoxy ethyl, 2-methoxy ethyl, and 2-ethoxy ethyl.

The α-cyanoacrylates of formula (I) may be prepared according to methods known in the art. U.S. Pat. Nos. 2,721,858 and 3,254,111, each of which is hereby incorporated in its entirety by reference, disclose methods for preparing α-cyanoacrylates. For example, the α-cyanoacrylates may be prepared by reacting an alkyl cyanoacetate with formaldehyde in a nonaqueous organic solvent and in the presence of a basic catalyst, followed by pyrolysis of the anhydrous intermediate polymer in the presence of a polymerization inhibitor.

The α-cyanoacrylates of formula (I) wherein $R^3$ is a group having the formula $R^4$—O—$R^5$—O—$R^6$ may be prepared according to the method disclosed in U.S. Pat. No. 4,364,876 to Kimura et al., which is hereby incorporated in its entirety by reference. In the Kimura et al. method, the α-cyanoacrylates are prepared by producing a cyanoacetate by esterifying cyanoacetic acid with an alcohol or by transesterifying an alkyl cyanoacetate and an alcohol; condensing the cyanoacetate and formaldehyde or para-formaldehyde in the presence of a catalyst at a molar ratio of 0.5-1.5:1, preferably 0.8-1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The α-cyanoacrylates of formula (I) wherein $R^3$ is a group having the formula

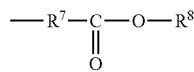

may be prepared according to the procedure described in U.S. Pat. No. 3,995,641 to Kronenthal et al., which is hereby incorporated in its entirety by reference. Examples of monomers of formula (I) include cyanopentadienoates and α-cyanoacrylates of the formula:

wherein Z is —CH═$CH_2$ and $R^3$ is as defined above. The monomers of formula (II) wherein $R^3$ is an alkyl group of 1-10 carbon atoms, i.e., the 2-cyanopenta-2,4-dienoic acid esters, may be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated in its entirety by reference.

Suitable α-cyanoacrylate monomers which may be used, alone or in combination, include alkyl α-cyanoacrylates such as 2-octyl cyanoacrylate; dodecyl cyanoacrylate; 2-ethylhexyl cyanoacrylate; butyl cyanoacrylate such as n-butyl cyanoacrylate; ethyl cyanoacrylate; methyl cyanoacrylate or other α-cyanoacrylate monomers such as methoxyethyl cyanoacrylate; 2-ethoxyethyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. In embodiments, the monomers are ethyl, n-butyl, or 2-octyl α-cyanoacrylate. Other cyanoacrylate monomers which may be used include alkyl ester cyanoacrylates, such as those prepared by the Knoevenagel reaction of an alkyl cyanoacetate, or an alkyl ester cyanoacetate, with paraformaldehyde, subsequent thermal cracking of the resultant oligomer and distillation.

Monomers prepared with low moisture content and essentially free of impurities (e.g., surgical grade) are preferred for biomedical use. Monomers utilized for industrial purposes need not be as pure.

The alkyl ester cyanoacrylate monomers may have the formula:

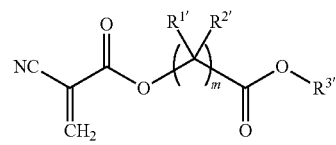

wherein $R^{1'}$ and $R^{2'}$ are, independently, H, a straight, branched or cyclic alkyl, or are combined together in a cyclic alkyl group, $R^{3'}$ is a straight, branched or cyclic alkyl group, and m is 1-8. Preferably, $R^{1'}$ is H or a $C_1$, $C_2$ or $C_3$ alkyl group, such as methyl or ethyl; $R^{2'}$ is H or a $C_1$, $C_2$ or $C_3$ alkyl group, such as methyl or ethyl; $R^{3'}$ is a $C_1$-$C_{16}$ alkyl group, more preferably a $C_1$-$C_{10}$ alkyl group, such as methyl, ethyl, propyl, isopropyl, butyl, isobutyl, pentyl, hexyl, heptyl, octyl, nonyl or decyl, and even more preferably a $C_2$, $C_3$ or $C_4$ alkyl group, and m is preferably 1-4.

Examples of the alkyl ester monomers may include, but are not limited to:

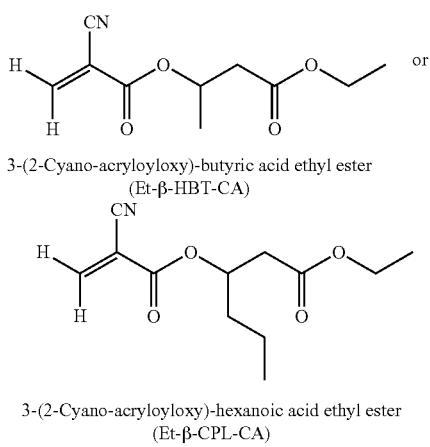

3-(2-Cyano-acryloyloxy)-butyric acid ethyl ester
(Et-β-HBT-CA)

3-(2-Cyano-acryloyloxy)-hexanoic acid ethyl ester
(Et-β-CPL-CA)

Additional examples of alkyl ester cyanoacrylate monomers include, but are not limited to, butyl lactoyl cyanoacrylate (BLCA), butyl glycoloyl cyanoacrylate (BGCA), isopropyl glycoloyl cyanoacrylate (IPGCA), ethyl lactoyl cyanoacrylate (ELCA), and ethyl glycoloyl cyanoacrylate (EGCA) and combinations thereof. BLCA may be represented by the formula above, wherein $R^{1'}$ is H, $R^{2'}$ is methyl and $R^{3'}$ is butyl. BGCA may be represented by the formula above, wherein $R^{1'}$ is H, $R^{2'}$ is H and $R^{3'}$ is butyl. IPGCA may be represented by the formula above, wherein $R^{1'}$ is H, $R^{2'}$ is H and $R^{3'}$ is isopropyl. ELCA may be represented by the formula above, wherein $R^{1'}$ is H, $R^{2'}$ is methyl and $R^{3'}$ is ethyl. EGCA may be represented by the formula above, wherein $R^{1'}$ is H, $R^{2'}$ is H and $R^{3'}$ is ethyl.

Other examples of alkyl ester cyanoacrylate monomers include alkyl alpha-cyanoacryloyl caprolactate and alkyl alpha-cyanoacryloyl butrylactate. Other cyanoacrylates useful in the present invention are disclosed in U.S. Pat. No. 3,995,641 to Kronenthal et al., the entire disclosure of which is hereby incorporated by reference.

Alternatively, or in addition, alkyl ether cyanoacrylate monomers may be used. Alkyl ethyl cyanoacrylates have the general formula:

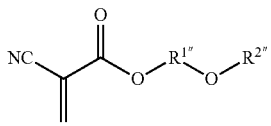

wherein $R^{1'''}$ is a straight, branched or cyclic alkyl, and $R^{2'''}$ is a straight, branched or cyclic alkyl group. Preferably, $R^{1'''}$ is a $C_1$, $C_2$ or $C_3$ alkyl group, such as methyl or ethyl; and $R^{2'''}$ is a $C_1$-$C_{16}$ alkyl group, more preferably a $C_1$-$C_{10}$ alkyl group, such as methyl, ethyl, propyl, isopropyl, butyl, isobutyl, pentyl, hexyl, heptyl, octyl, nonyl or decyl, and even more preferably a $C_2$, $C_3$ or $C_4$ alkyl group.

Examples of alkyl ether cyanoacrylate monomers include, but are not limited to, isopropyoxy ethyl cyanoacrylate (IPECA) and methoxy butyl cyanoacrylate (MBCA) or combinations thereof. IPECA may be represented by the formula above, wherein $R^{1'''}$ is ethylene and $R^{2'''}$ is isopropyl. MBCA may be represented by the formula above, wherein $R^{1'''}$ is n-butylene and $R^{2'''}$ is methyl.

Alkyl ester cyanoacrylate monomers and alkyl ether cyanoacrylate monomers are particularly useful for medical applications because of their absorbability by living tissue and associated fluids. The terms "absorbable" or "absorbable adhesive" or variations thereof refer to the ability of a tissue-compatible material to degrade or biodegrade at some time after implantation into products that are eliminated from the body or metabolized therein. Thus, as used herein, absorbability means that the polymerized adhesive is capable of being absorbed, either fully or partially, by tissue after application of the adhesive.

Likewise, the terms "non-absorbable" or "non-absorbable adhesive" or variations thereof refer to completely or substantially incapable of being absorbed, either fully or partially, by tissue after application of the adhesive. Furthermore, relative terms such as "faster absorbing" and "slower absorbing" are used relative to two monomer species to indicate that a polymer produced from one monomer species is absorbed faster (or slower) than a polymer formed from the other monomer species.

As used herein, the term "substantially absorbed" refers to at least 90% absorbed within about three years. Likewise, the term "substantially non-absorbed" means at most 20% absorbed within about three years. Preferably, 100% of the polymerized and applied cyanoacrylate when using these types of cyanoacrylate monomers may be absorbed in a period of less than 3 years, preferably approximately 2-24 months, more preferably 3-18 months, and most preferably 6-12 months after application of the adhesive to living tissue. The absorption time may vary depending on the particular uses and tissues involved. Thus, for example longer absorption time may be desired where the adhesive composition is applied to hard tissues, such as bone, but a faster absorption time may be desired where the adhesive composition is applied to softer tissues.

The selection of cyanoacrylate monomer will affect the absorption rate of the resultant polymer, as well as the polymerization rate of the monomer. Two or more different monomers that have varied absorption and/or polymerization rates may be used in combination to give a greater degree of control over the absorption rate of the resultant polymer, as well as the polymerization rate of the monomer.

The adhesive composition of the frangible container may comprise a mixture of cyanoacrylate monomers species with varying absorption rates. Where two monomer species having different absorption rates are used, it is preferred that the absorption rates be sufficiently different that a mixture of the two monomers may yield a third absorption rate that is effectively different from the absorption rates of the two monomers individually. Compositions according to these embodiments are described, for example, in U.S. patent application Ser. No. 09/919,877, filed Aug. 2, 2001, published as U.S. Patent Publication No. 2002/0037310 on Mar. 28, 2002, and U.S. Pat. No. 6,620,846, both incorporated herein by reference in their entireties.

Absorbable cyanoacrylate monomers have broad application for closure and hemostatic sealing of wounds and the like in various living tissue, including but not limited to internal organs and blood vessels. These absorbable formulations may be applied on the interior or exterior of various organs and tissues. Adhesives as disclosed are biocompatible and may be applied internally or externally in or on living tissue.

For example, suitable adhesive compositions for the frangible container may be prepared by mixing suitable quantities of an alkyl alpha cyanoacrylate such as 2-octyl alpha-cyanoacrylate with one of butyl lactoyl cyanoacrylate (BLCA), butyl glycoloyl cyanoacrylate (BGCA), isopropyl glycoloyl cyanoacrylate (IPGCA), ethyl lactoyl cyanoacrylate (ELCA), and ethyl glycoloyl cyanoacrylate (EGCA). Such mixtures may range from ratios of about 90:10 to about 10:90 by weight, preferably about 75:25 to about 25:75 by weight such as from about 60:40 to about 40:60 by weight.

In embodiments, the applicator device may contain materials such as a polymerization initiator, accelerator, rate-modifier, and/or cross-linking agent for initiating polymerization and/or cross-linking of the polymerizable monomer material. The polymerization initiator, accelerator, rate-modifier, and/or cross-linking agent may be incorporated into the retaining member and/or filter, the flow restrictor and/or the reservoir of the applicator device.

Accelerated polymerization reduces the waiting time necessary after application, and makes the adhesive composition more convenient to apply. Useful polymerization initiators or accelerators may include those suitable for medical applications. For purposes herein, the phrase "suitable for medical application(s)" means that the polymerization of the monomer occurs in less than 5 minutes or less than 3 minutes, preferably in less than 2.5 minutes, more preferably in less than 1 minute, and often in less than 45 seconds. Of course, the desired polymerization time can vary for different compositions and/or uses. Preferably, where absorbability is desired, a suitable initiator or accelerator and a suitable monomer are selected to provide a polymer that is substantially absorbed by a living organism in 2-24 months, such as 3-18 months or 6-12 months after application of the adhesive to living tissue. In embodiments where an initiator and/or accelerator is used, such agent is preferably located in a non-contacting relationship with the adhesive composition prior to use, so that premature polymerization of the adhesive composition does not occur.

Suitable initiators are known in the art and are described, for example, in U.S. Pat. Nos. 5,928,611 and 6,620,846, both incorporated herein by reference in their entireties, and U.S. Patent Application No. 2002/0037310, also incorporated herein by reference in its entirety. Quaternary ammonium chloride and bromide salts useful as polymerization initiators are particularly suitable. By way of example, quaternary ammonium salts such as domiphen bromide, butyrylcholine chloride, benzalkonium bromide, acetyl choline chloride, among others, may be used.

Benzalkonium or benzyltrialkyl ammonium halides such as benzyltrialkyl ammonium chloride may be used in addition to one or more quaternary ammonium fluoride salts or one or more quaternary ammonium ether salts. When used, the benzalkonium halide may be benzalkonium halide in its unpurified state, which comprises a mixture of varying chain-length compounds, or it can be any suitable purified compound including those having a chain length of from about 12 to about 18 carbon atoms, including but not limited to $C_{12}$, $C_{13}$, $C_{14}$, $C_{15}$, $C_{16}$, $C_{17}$, and $C_{18}$ compounds. By way of example, the additional initiator may be a quaternary ammonium chloride salt such as benzyltrialkyl ammonium chloride (BTAC).

Other initiators or accelerators may also be selected by one of ordinary skill in the art without undue experimentation. Such suitable initiators or accelerators may include, but are not limited to, detergent compositions; surfactants: e.g., non-ionic surfactants such as polysorbate 20 (e.g., Tween 20™ from ICI Americas), polysorbate 80 (e.g., Tween 80™ from ICI Americas) and poloxamers, cationic surfactants such as tetrabutylammonium bromide, anionic surfactants such as sodium tetradecyl sulfate, and amphoteric or zwitterionic surfactants such as dodecyldimethyl(3-sulfopropyl)ammonium hydroxide, inner salt; amines, imines and amides, such as imidazole, arginine and povidine; phosphines, phosphites and phosphonium salts, such as triphenylphosphine and triethyl phosphite; alcohols such as ethylene glycol, methyl gallate; tannins; inorganic bases and salts, such as sodium bisulfite, calcium sulfate and sodium silicate; sulfur compounds such as thiourea and polysulfides; polymeric cyclic ethers such as monensin, nonactin, crown ethers, calixarenes and polymeric-epoxides; cyclic and acyclic carbonates, such as diethyl carbonate; phase transfer catalysts such as Aliquat 336; organometallics such as cobalt naphthenate and manganese acetylacetonate; and radical initiators or accelerators and radicals, such as di-t-butyl peroxide and azobisisobutyronitrile.

In embodiments, anti-microbial or therapeutic agents may be included with the polymerization adhesive composition.

In embodiments where monomer additives including, but not limited to those listed above, are insoluble with the monomer composition and/or that would cause premature polymerization of the monomer, the additive may be applied to the application site before applying the monomer composition. In such embodiments, the additive may be provided, for example, in separate packages in a kit.

In other embodiments, where such additives are soluble with the polymerizable adhesive composition and/or would not cause premature polymerization, the additives may be combined with the polymerizable adhesive composition during its manufacture.

The additive may be mixed immediately prior to use upon rupture of the cartridge, ampoule or ampoules by activation of the annular collar or housing. Alternatively, mixing may be conducted in the reservoir and/or during the application process, for example, which thereby mixes the additive with the adhesive composition during application. In addition, as discussed above with respect to suitable anti-microbial and therapeutic agents, other additives may serve as stabilizers for the adhesive composition.

The adhesive composition may optionally include at least one plasticizing agent that assists in imparting flexibility to the polymer formed from the polymerizable adhesive composition. The plasticizing agent preferably contains little or no moisture and should not significantly affect the stability or polymerization of the polymerizable adhesive composition. Examples of suitable plasticizers include acetyl tributyl citrate, dimethyl sebacate, dibutyl sebacate, triethyl phosphate, tri(2-ethylhexyl)phosphate, tri(p-cresyl)phosphate, glyceryl triacetate, glyceryl tributyrate, diethyl sebacate, dioctyl adipate, isopropyl myristate, butyl stearate, lauric acid, trioctyl trimellitate, dioctyl glutarate, polydimethylsiloxane, and mixtures thereof. Preferred plasticizers may include tributyl citrate, acetyl tributyl citrate or dibutyl sebacate. In embodiments, suitable plasticizers include polymeric plasticizers, such as polyethylene glycol (PEG) esters and capped PEG esters or ethers, polyester glutarates and polyester adipates, as well as others as listed in U.S. Pat. No. 6,183,593, the disclosure of which is incorporated in its entirety by reference herein.

The adhesive composition may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. No. 4,720,513, and U.S. Pat. No. 6,310,166, the disclosures of which are hereby incorporated in their entireties by reference herein.

The adhesive composition may optionally also include thickeners. Suitable thickeners may include poly (L-lactide-co-caprolactone), poly(2-ethylhexy methacrylate), poly(2-ethylhexyl acrylate) and others as listed in U.S. Pat. No. 6,673,192, the disclosure of which is incorporated by reference herein in its entirety.

The adhesive composition may also optionally include at least one natural or synthetic rubber to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The adhesive composition may optionally also include one or more stabilizers, including one or more free radical stabilizers and/or one or more anionic stabilizers, preferably both at least one anionic vapor phase stabilizer and at least one anionic liquid phase stabilizer. These stabilizing agents may inhibit premature polymerization. Suitable stabilizers may include those listed in U.S. Pat. No. 6,183,593, the disclosure of which is incorporated by reference herein in its entirety. Furthermore, certain stabilizers may also function as anti-microbial agents, such as, for example, various acidic anti-microbials, as identified above.

The stability, and thus the shelf-life, of some monomeric adhesive compositions may be further enhanced and extended through careful regulation of the ampoule. Treated (e.g., fluorinated polymer) glass ampoules may reduce the amount of stabilizer that is combined into the adhesive composition. As mentioned above, certain stabilizers including, but not limited to, certain acidics may also function as anti-microbial agents. In this case, the amount of the anti-microbial/stabilizer material is either not reduced below a level to provide the desired anti-microbial effect, or a further anti-microbial/non-stabilizing agent is added to ensure that the desired anti-microbial effect is provided.

The adhesive compositions may also include pH modifiers to control the rate of degradation of the resulting polymer, as disclosed in U.S. Pat. No. 6,143,352, the entire disclosure of which is hereby incorporated by reference herein in its entirety.

To improve the cohesive strength of adhesives formed from the adhesive compositions applicable to the applicator device herein described, difunctional monomeric cross-linking agents may be added to the monomer compositions. Such crosslinking agents include those as disclosed in U.S. Pat. No. 3,940,362, which is hereby incorporated herein in its entirety by reference, discloses exemplary cross-linking agents.

The adhesive compositions of this invention may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593, the disclosure of which is incorporated by reference herein in its entirety.

The polymerizable compositions useful in the present invention may also further contain one or more preservatives, for prolonging the storage life of the adhesive composition. Suitable preservatives, and methods for selecting them and incorporating them into adhesive compositions, are disclosed in U.S. Pat. No. 6,579,469, the entire disclosure of which is incorporated herein by reference.

In embodiments, the adhesive applicator, including its monomer composition and/or its packaging may be sterilized. However, sterilization is not required, particularly in view of the fact that the adhesive composition will be used on open wounds. Furthermore, whether or not the applicator is sterilized, the applicator adhesive composition may further include one or more suitable preservatives, as described below.

Sterilization of the applicator monomer composition and/or its packaging may be accomplished by techniques known to the skilled artisan, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation, as described in U.S. Pat. No. 6,143,805, the entire disclosure of which is incorporated herein by reference. The different components or groups of components of the applicator may be sterilized separately before packaging or assembly of the components or groups of components, and/or the different components or groups of components may be sterilized after assembly or packaging as is disclosed in co-assigned U.S. Pregrant Patent Publication No. 2004/0120849, which is hereby incorporated herein in its entirety by reference. The materials of the applicator and/or the adhesive composition should also show low levels of toxicity to living tissue during its useful life. In preferred embodiments of the present invention, the applicator and/or adhesive composition is sterilized to provide a Sterility Assurance Level (SAL) of at least $10^{-3}$. In embodiments, the Sterility Assurance Level may be at least 10, or may be at least $10^{-5}$, or may be at least $10^{-6}$.

The materials used for the construction of the applicator device may contain antimicrobials which migrate to the surface of the applicator device to provide antimicrobial action or prevent or eliminate microbial colonization during use. Such antimicrobials include, but are not limited to, triclosan, chlorhexidine, silver sulfadiazine, silver salts, hinokitiol, benzalkonium chloride and zinc pyrithione. Antimicrobials may be added to the materials comprising the applicator device such as the body portion, reservoir and/or actuator during the molding process or may be impregnated or applied after the applicator device or its components are molded, and includes impregnation or application before or after assembly.

In addition to the various advantages identified above, the applicator device and methods of using same provide additional advantages over state-of-the art adhesive application protocols. For example, an advantage of using the applicator in combination with a polymerizable adhesive compositions such as monomeric cyanoacrylate is that the adhesive compositions polymerize on contact with the site, forming an occlusive dressing and creating a moist wound environment conducive to healing. Healing of such injured site is thus expected to be quicker and more natural than for other treatment protocols. Furthermore, this occlusive coating protects the site from further injury while also functioning as a microbial barrier.

Still further, the present invention provides adhesive application protocols that are considered advantageous both to the healthcare professional and the patient. In the clinical scenario, use of applicator containing topically applied polymerizable adhesive compositions, such as monomeric cyanoacrylate, in frangible ampoules may pose the possibility of leakage of the adhesive from the applicator remote from the wound site. The applicator herein described provides for sealed containment of the adhesive and improved control of its application at the wound site.

In embodiments, the applicator device may be used and/or packaged in combination with a flexible material such as a mesh. The flexible material may comprise a polymerization initiator or rate modifier disposed in or on the flexible material. The applicator device may provide for the polymerizable adhesive composition to be applied and permeated throughout at least a portion of the flexible material, where the polymerization initiator or rate modifier is a polymerization initiator or rate modifier for the polymerizable adhesive composition. The flexible material may be a tissue bonding article for bonding tissue surfaces, or may be used in other applications.

The flexible material may be applied to a surface, and impregnated with a polymerizable monomeric adhesive composition from the applicator device, which upon setting or curing provides an adherent structure over the surface. Polymerization (setting or curing) of the polymerizable monomeric adhesive composition is assisted by the flexible material being loaded, coated, or the like with a polymerization initiator or rate modifier for the polymerizable monomeric adhesive composition.

The flexible material preferably includes one or more chemical materials located within the flexible material. For example, one or more chemical substances may be dispersed in the flexible material, such as being chemically bound, physically bound, absorbed, or adsorbed to the flexible material. Thus, for example, the flexible material preferably includes at least a polymerization initiator or rate modifier, and may optionally include one or more bioactive materials. As desired, the one or more chemical substances may be either immobilized on or in the flexible material, for example, so that it has a desired effect but is not detached from the flexible material during use, or it may be attached to the flexible material in a manner such that it becomes detached during use.

For example, a polymerization initiator or rate modifier may be loaded on the flexible material so that the initiator or rate modifier provides the desired initiation or rate modification effect to a subsequently applied polymerizable adhesive composition. The polymerization initiator or rate modifier may be immobilized on the flexible material, so that the initiator or rate modifier does not become detached from the flexible material and its residues dispersed in the resultant polymeric material. Alternatively, for example, the polymerization initiator or rate modifier may be initially attached to the flexible material, but only in such a manner that it becomes mobilized or solubilized by a subsequently applied polymerizable adhesive composition and dispersed in the resultant polymeric material.

If desired, a combination of chemical substances may also be provided on the flexible material, to provide multiple effects. For example, as described above, a first chemical species (such as a polymerization initiator or rate modifier) may be immobilized on the flexible material, while a second, different chemical species (such as a bioactive material) may be detachably attached to the flexible material. Other combinations of chemical species and resultant effects are also envisioned.

When present in or on the flexible material, the chemical substances (i.e., polymerization initiator, rate modifier, and/or bioactive materials, or other additives), may be incorporated in or on the flexible material in any suitable manner. For example, the chemical substance may be added to the flexible material by contacting the flexible material with a solution, mixture, or the like including the chemical substances. The chemical substance may be added to the flexible material, for example, by dipping, spraying, roll coating, gravure coating, brushing, vapor deposition, or the like. Alternatively, the chemical substance may be incorporated into or onto the flexible material during manufacture of the flexible material, such as during molding or the like of the flexible material.

The chemical substance may be present in or on the flexible material in any suitable concentration and manner. For example, the chemical substance may be applied in a uniform manner to the flexible material, such that there is a substantially uniform concentration of the chemical substance across the flexible material. Alternatively, the chemical substance may be applied such that a concentration gradient exists across or through the flexible material. For example, a greater or smaller concentration of the chemical substance could exist at the center or edges of the flexible material, or a greater or smaller concentration of the chemical substance could be applied on one side of the flexible material as compared to an opposite side. Further, the chemical substance may be applied in a uniform manner to the flexible substrate, or it may be applied in a non-uniform random or patterned manner (such as lines, dots, concentric circles, or the like).

Other chemical substances that may be present in or on the flexible material include, but are not limited to, any suitable and preferably compatible additive that enhances performance of the composite structure. Such additional chemical substances may be bioactive or non-bioactive. Suitable other chemical substances thus include, but are not limited to, colorants (such as inks, dyes and pigments), scents, protective coatings that do not chemically detach, temperature sensitive agents, drugs, and the like.

The polymerization initiator or rate modifier loaded on the flexible material may provide a number of advantages for example, the tailoring of the setting or polymerization time of the applied polymerizable adhesive composition. For example, the type and/or concentration of initiator that is applied to the flexible material may be selected so as to provide faster or slower polymerization time. The concentration of polymerization initiator or rate modifier may be increased to provide a faster polymerization time, or may be decreased to provide a slower polymerization time.

Because the polymerization initiator or rate modifier is loaded directly on the flexible material, it is not necessary to mix the polymerizable adhesive composition with a polymerization initiator or rate modifier in an applicator prior to application. Thus, the applicator device containing the polymerizable adhesive composition may avoid or eliminate becoming plugged and unusable by polymerizable adhesive composition polymerizing in an applicator tip. This may allow a longer working time, where the polymerizable monomer composition may be more precisely and carefully applied over a longer period of time.

The flexible material may trap or act as a barrier to flow of the polymerizable adhesive composition during application, therefore there may be less running of the adhesive composition away from the application site. In addition, where one or more chemical substances are present in or on the flexible material, such chemical substances may be more specifically or precisely applied. For example, the chemical substances may be applied to the flexible material only at specific locations, or in a gradient pattern, if desired, which may provide a stronger composite structure than is provided by a polymerizable adhesive composition alone.

The flexible or compliant material may be formed of any suitable flexible or compliant material. Preferably, the flexible or compliant material is a material that is flexible, porous, and non-toxic. Suitable flexible materials are as described in co-assigned U.S. Pregrant Patent Application No. 2006/0009099, incorporated herein by reference in its entirety.

The flexible material is preferably flexible or compliant, to allow the flexible substrate to be placed on the desired surface (such as skin, organ, tissue, or the like) in a manner that allows the flexible substrate to conform to the topology of the desired surface. Likewise, the flexible material is preferably porous, to allow the subsequently applied polymerizable adhesive material to pass through or permeate through the flexible material and to polymerize as a layer beneath the flexible material, while adhering the flexible material to the desired substrate. By "porous" is meant herein either that the bulk of the flexible material has pores, such that the subsequently applied polymerizable adhesive material is soaked up or absorbed by the bulk material, or that the bulk of the flexible material has voids (like a net or screen), such that the subsequently applied polymerizable adhesive material passes directly through the bulk material, with or without being soaked up or absorbed by the bulk material. For example, in the case of textile materials, "porous" is generally used to mean that the applied adhesive composition permeates and passes through interstices between the fibers, but does not necessarily pass into and through the fibers themselves.

Such porosity (or other properties such as hydrophobicity or hydrophilicity) will also allow a polymerization initiator or rate modifier to be loaded on the flexible material prior to use, to initiate the subsequently applied polymerizable adhesive material. Such porosity will also preferably allow air and water to pass through the flexible material (either through pores per se, or through voids in the bulk material). Depending upon the degree of porosity (and/or the size of the openings), such porosity of the flexible material or ability of air and water to permeate through the flexible material may be tailored to either remain after a final composite material is formed, or to be absent therefrom. The flexible material is also preferably non-toxic, as it is intended to be used as a wound covering, such as on biological tissues. As such, the flexible material should be biologically compatible with the desired substrate (such as tissue, skin, organ, or the like), and is preferably a material that is governmentally approved or generally regarded as safe for the desired purpose.

In embodiments, the flexible material is a textile or mesh/web material. Suitable textile materials may be formed of either synthetic or natural materials. Such textile material may be formed of either woven or non-woven fabrics or materials. The flexible material may be, for example, any suitable polymeric film, plastic foam (including open celled foam), a woven fabric, knitted fabric, a non-woven fabric, mixture thereof, or the like. In particular, suitable flexible materials may thus be prepared, for example, from nylon, a polyolefin film, such as polyethylene, polypropylene, ethylene propylene copolymers, and ethylene butylene copolymers, polyurethanes, polyurethane foams, polystyrenes, plasticized polyvinylchlorides, polyesters, polyamides, polylactic acid, polyglycolic acid, polycaprolactone, copolymer mixtures of the above, and cotton. Suitable specific examples include, for example, nylon, polyethylene, polypropylene, ethylene propylene copolymers, ethylene butylene copolymers, polyurethane, polystyrene, plasticized polyvinylchloride, polyester, polyamide, cotton, polytetrafluoroethylene (PTFE), biovascular material, collagen, Gore-Tex®, DACRON®, etc.

The flexible material may be formed of a synthetic, semi-synthetic, or natural organic material. Thus, for example, the flexible material may be formed of a synthetic or natural polymer material, but not from a material such as metal (such as silver, steel or the like) or glass or ceramic. The flexible material may be either biodegradable, or not biodegradable. The flexible material is preferably resistant to tearing. The thickness of the flexible material may be from about 0.1 mil to about 80 mils. In another embodiment, the thickness of the flexible material is from about 0.5 mil to about 20 mils, preferably from about 0.7 mil to about 10 mils, or from about 1 mil to about 5 mils.

The size of the flexible material may be tailored for specific intended uses, or it may be provided in a sheet or roll form or any suitable shape or dimension of the flexible material may be provided. The flexible material may be provided in a dispenser. The flexible material is not limited to any particular dimensions, and the dimensions (length, width, thickness, etc.) of the flexible material may be varied and tailored, as desired.

In some embodiments, the flexible material can include a pressure sensitive adhesive on at least one face, by way of example, to assist in initial placement of the flexible material on the desired surface. In embodiments where the flexible material includes a pressure sensitive adhesive applied to portions of the flexible material, the pressure sensitive adhesive can be applied to an entire surface of the flexible material, or only to portions (such as peripheral edges) of the surface of the flexible material. The exposed pressure sensitive adhesive can be covered by a suitable release layer or liner, if desired, to preserve the adhesiveness of the flexible material until time of use. The pressure sensitive adhesive, if present, can be applied in the various manners shown in U.S. Patent Application Publication No. 2005/0182443, the entire disclosure of which is incorporated herein by reference.

In embodiments, a method of bonding tissue is provided. The method comprises placing a flexible material over a substrate, the flexible material comprising a polymerization initiator or rate modifier disposed in or on the flexible material. The applicator device as herein described applies a polymerizable adhesive composition over and substantially covering at least a portion of the flexible material. The polymerizable adhesive composition is allowed to permeate into and under the flexible material and polymerize to form a composite structure bonded to the substrate. The substrate may be tissue. The tissue may be hard tissue (such as bone) or soft tissue (such as skin, organs, mucous membranes, and the like). The tissue may be either internal or external.

In other embodiments, a kit is provided. The kit comprises: at least one applicator device as herein described; and optionally one or more containers of adhesive or sealant material arranged to be placed at least partially in the cavity of the at least one applicator device, wherein movement of the actuator relative to the body portion deflects the breaking member to rupture one of the containers that is placed at least partially in the cavity. In embodiments, the kit further comprises a plurality of removable and/or interchangeable applicator tips. In embodiments, the kit further comprises a flexible material/mesh which may be loaded with polymerization initiator or rate modifier for the adhesive or sealant material. The different components or groups of components may be sterilized in separate containers before packaging the components or groups of components within a kit, and thereafter sterilizing the kit as disclosed in co-assigned U.S. Pregrant Patent Publication No. 2004/0120849.

Various other features and advantages of the embodiments of the invention will be apparent from the following description of exemplary embodiments and figures.

Referring to FIG. 1, applicator device 10 includes body portion 100 having a closed proximal end 110. Actuator 300 includes annular collar 301, which mechanically secures body portion 100 with reservoir 600. Reservoir 600 includes distal applicator tip 620 for dispensing of adhesive.

Figure 2:
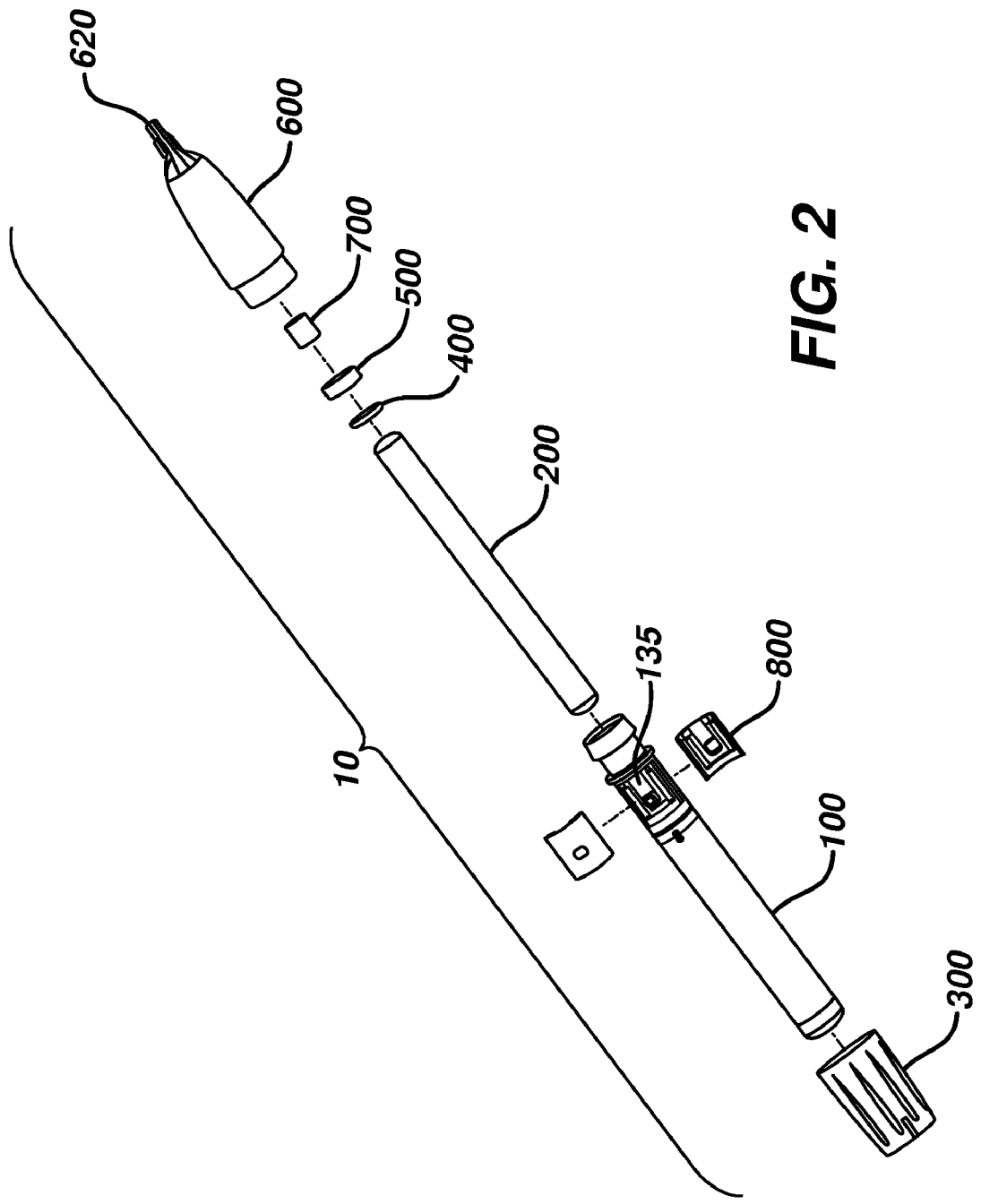
FIG. 2 is an exploded view of the embodiment as shown in FIG. 1.

Referring now to FIG. 2, applicator device 10 includes frangible container 200, which is contained in body 100 and in proximity to breaking member 135 of body portion 100.

Semi-rigid section 800 overlays breaking member in sealable contact therewith. Filter 400 and retaining member 500 separate frangible container 200 from reservoir 600. Reservoir 600 includes flow restrictor 700, which is frictionally secured at reservoir 600 distal end of applicator tip 620.

Figure 3:
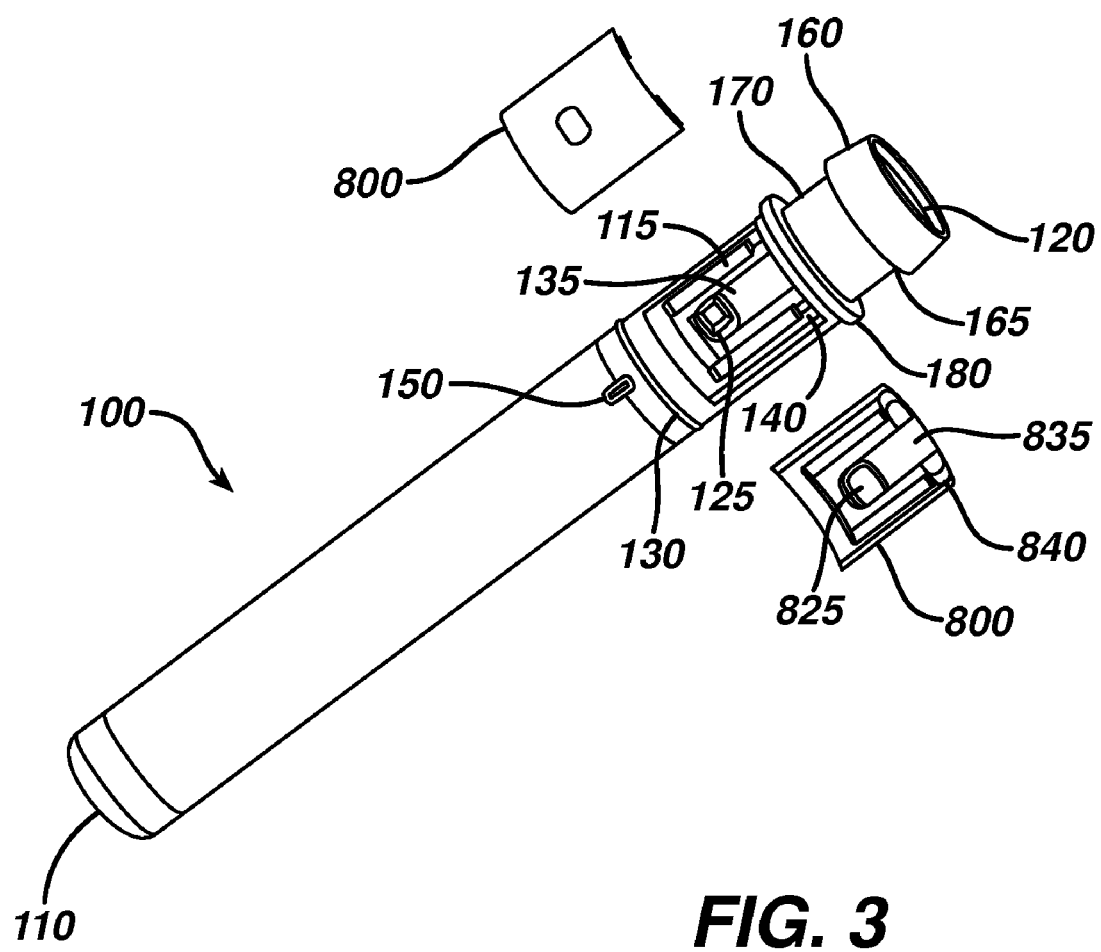
FIG. 3 is an exploded view of the body portion of the embodiment as shown in FIG. 1.

Referring now to FIG. 3, breaking member 135 of body portion 100 is positioned in surrounding gap 115 between closed proximal end 110 and open distal end 120 to provide for deflection into the cavity. First engagement member 125 of breaking member 135 projects outwardly from the body portion. Semi-rigid section 800 seals surrounding gap 115 and sealably contacts breaking member 135 via section 835. Semi-rigid section 800 includes orifice 825 for exposing first engagement member 125 through the semi-rigid section. Undercut 140 in body portion 100 accepts and mates with protrusions 840 of semi-rigid section 800 to provide leak-resistant sealing.

Figure 4:
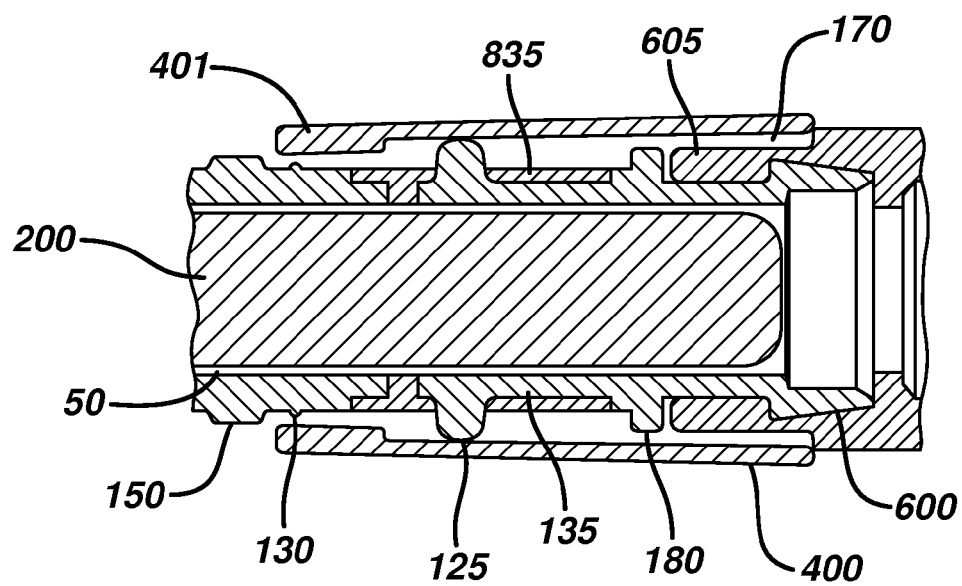
FIG. 4 is a sectional view of the body portion and annular housing embodiment depicting non-engagement of corresponding engaging members of an embodiment of FIG. 2.
Figure 5:
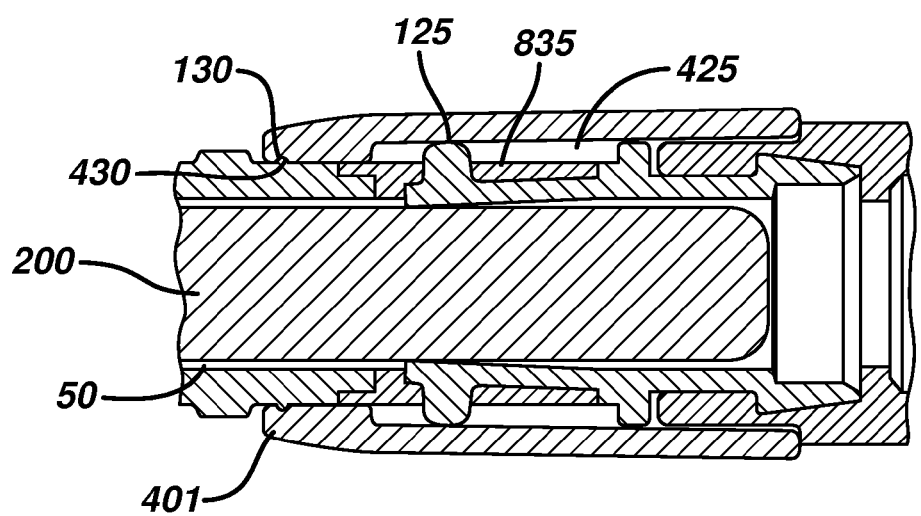
FIG. 5 is a sectional view of body portion and annular housing embodiment depicting engagement of corresponding engaging members of an embodiment of FIG. 2.

Referring to FIGS. 3, 4 and 5, forward tapered collar 160 with undercut 165 provides for accepting the reservoir flange 605 into recess 170 which may extend up to and abut forward lip 180. Reservoir 600 is mechanically secured to body portion 100 between annular collar 401 and recess 170 and forward tapered collar 160. Annular groove 430 of actuator 400 receives annular rib 130 of body portion 100 to secure the actuator on body portion.

Figure 7:
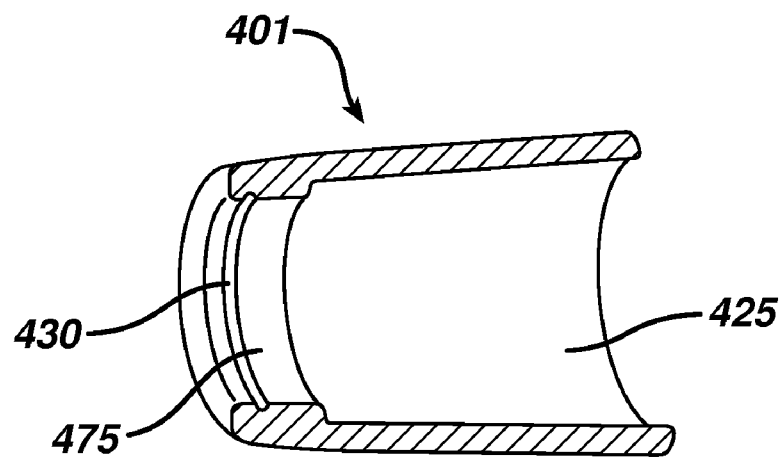
FIG. 7 is a sectional view of an actuator embodiment.

Still referring to FIGS. 4 and 5, the first and second positions of the actuator are depicted. In a first position, second engagement members 425 (not shown) of annular collar 401 are disengaged with the first engagement members 125 of breaking members 135, as shown in FIG. 4. In a second position, second engagement members 425, shown as a thickened wall section, of annular collar 401 are engaged with first engagement members 125 of breaking members 135 causing deflection of the breaking members into frangible container 200 in the cavity 50 as shown in FIG. 5. Deflection into the cavity is such that a frangible container 200 would be ruptured to release its contents. Body portion indexing marker 150 provides for indexing of actuator 400 for assembly without engaging first and second engagement members. During assembly, annular groove 430 snaps over annular rib 130 and then upon assembly relaxes around annular rib 130 as shown assembled in FIG. 5. Sectional view of actuator 400, as shown in FIG. 7, depicts indexing track element 475 for positioning and receiving indexing body portion indexing marker 150 during assembly.

Figure 6:
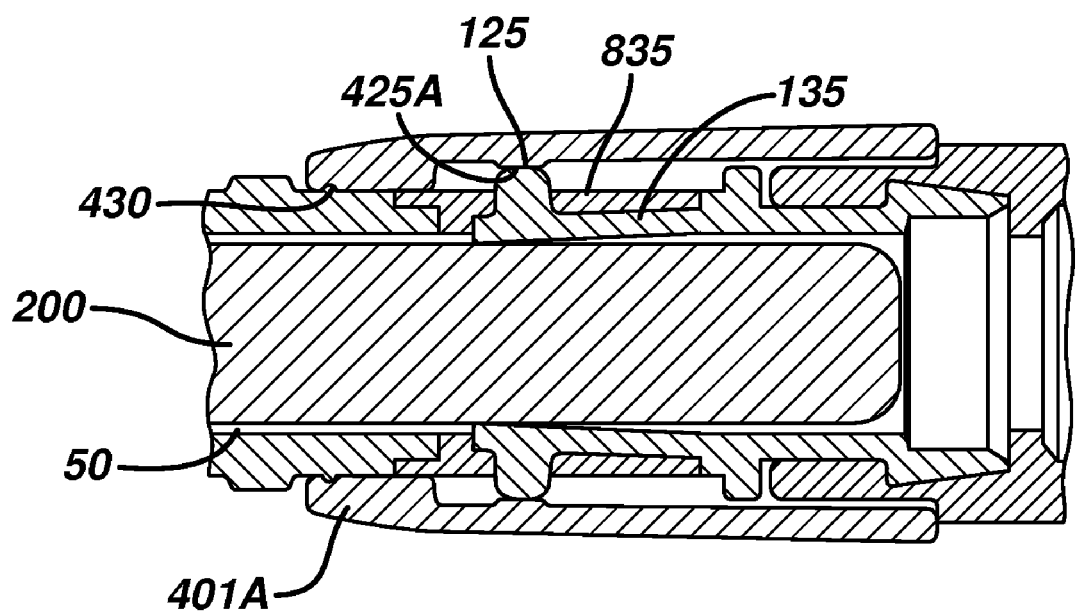
FIG. 6 is a sectional view of body portion and annular housing depicting engagement of corresponding engaging members of an embodiment of FIG. 2.

Referring now to FIG. 6, a second position of an embodiment of an actuator is depicted. In a second position, second engagement members 425A, shown as cam elements, of annular collar 401A are engaged with first engagement members 125 of breaker members 135 causing deflection of the breaking members into the frangible container 200 in the cavity 50. Deflection into the cavity is such that a frangible container 200 would be ruptured to release its contents, as shown in FIG. 6.

Figure 8:
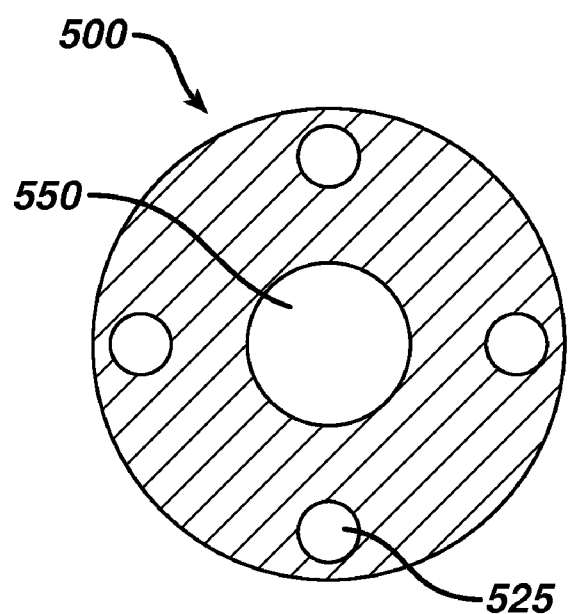
FIG. 8 is a top plan view of a retaining member of the embodiment as shown in FIG. 2.
Figure 9:
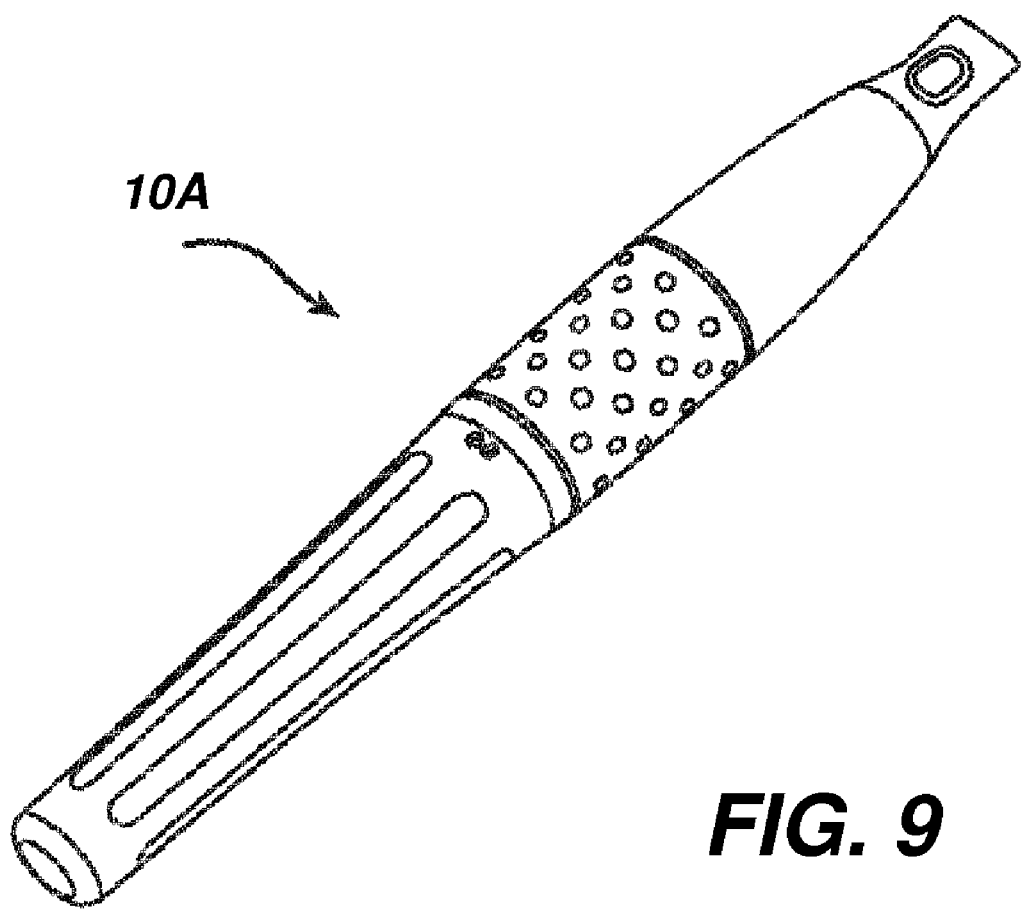
FIG. 9 is a top perspective view of an applicator device embodiment.
Figure 10:
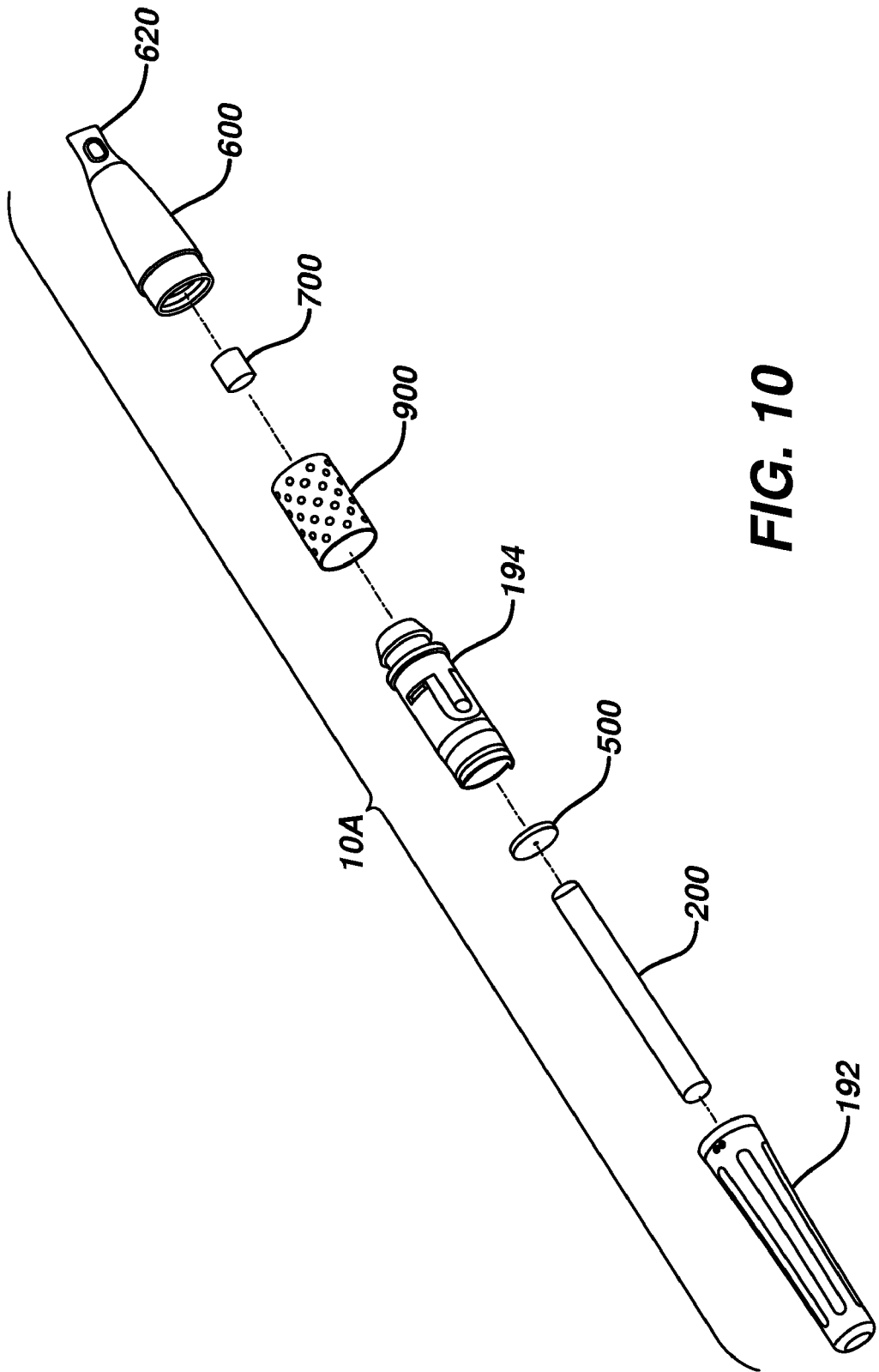
FIG. 10 is an exploded view of the embodiment as shown in FIG. 9

Referring now to FIG. 8, an exemplary retaining member 500 includes orifices 525 and larger orifice 550. Orifices 525 alone or in combination with filter 400 provide retention of the frangible container 200 within the cavity while larger orifice 550 provides for concurrent venting of the cavity.

Figure 11:
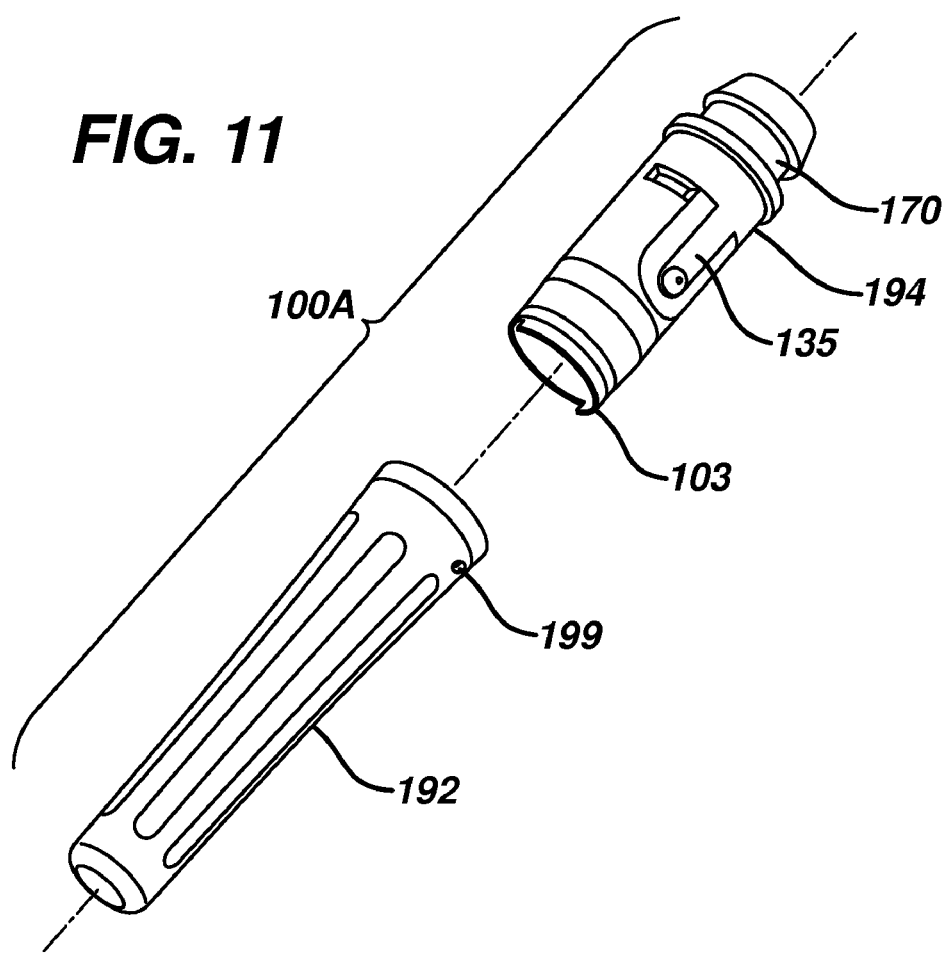
FIG. 11 is an exploded view of a body portion of the embodiment as shown in FIG. 9.
Figure 12:
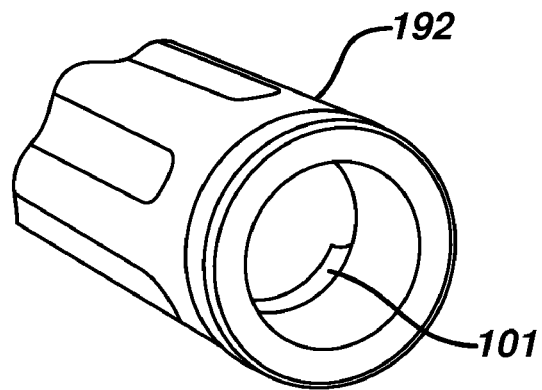
FIG. 12 is perspective view of a body segment of the embodiment as shown in FIG. 9.

Referring now to FIGS. 9-12, dispenser 10A includes body portion 100A, which includes forward body segment 194 and rearward body segment 192, as shown in FIG. 11 (annular housing not shown). Forward body segment 194 including breaking member 135 is received by rearward body segment 192 with cooperative alignment means 103 and 101. Retaining member 500 is positioned within forward body segment 194 securing frangible container 200 into body portion 100A.

Reservoir 600 includes flow restrictor 700 frictionally secured at the distal end of the reservoir. By way of example, dispenser 10A may be assembled by receiving forward body segment 194 into rearward body segment 192 with cooperative alignment means 103 and 101, placing the open proximal end of reservoir 600 over recess 170 of forward body segment 194 and sliding actuator 900 over forward body segment 194. Forward and rearward body segments 194, 192 of body portion 100A may be secured by placing a solvent or adhesive in one of securing orifices 199 in rearward body segment 192, for example, using a syringe, until solvent or adhesive comes out of the other orifice.

While the invention has been described with reference to preferred embodiments, the invention is not limited to the specific examples given, and other embodiments and modifications may be made by those skilled in the art without departing from the spirit and scope of the invention. Thus, while this invention has been described in terms of exemplary embodiments, it is to be understood that this invention is not to be limited to the particular configuration of these embodiments. One skilled in the art will recognize that various modifications and/or alterations of these embodiments may be made while remaining within the scope of this invention.

What is claimed is:

1. A method of applying/dispensing an adhesive material, the method comprising:
   providing an applicator device for dispensing and/or applying an adhesive material, the applicator device comprising:
      a body portion comprising a closed proximal end and an open distal end providing a cavity;
      at least one breaking member integral with the body portion and each breaking member having a surrounding gap, the at least one breaking member at least partially deflectable into the cavity and each breaking member having a first engagement member;
      an annular housing movable with respect to the body portion and having a second engagement member complementary with the at least one first engagement member, the first and the second engagement member being cooperatively engageable with each other;
      a reservoir secured to the open distal end of the body portion, the reservoir further having a distal opening comprising applicator means,
      a retaining member between the body portion and the reservoir; and
      a frangible container of adhesive material disposed within the cavity between the closed proximal end and the retaining member;
   moving the annular housing relative to the body portion from a first position where the first and the second engagement member are not cooperatively engaged with each other, to a second position where the first and the second engagement member are cooperatively engaged with each other, deflecting at least a portion of the breaking member into the cavity breaking the frangible container;
   squeezing the reservoir providing a positive pressure within the reservoir and
   dispensing adhesive material from the reservoir to a substrate;
   wherein releasing the squeezed reservoir creates a negative pressure within the reservoir for urging of the adhesive material from the cavity into the reservoir.

2. The method of claim 1, wherein the substrate is living tissue, a flexible material or mesh.

3. The method of claim 2, wherein the flexible material or mesh comprises at least one of a medicament, a polymerization initiator or polymerization rate modifier for the adhesive material.

4. The method of claim 2, wherein the applicator device, the frangible container of adhesive material and/or the adhesive material is sterilized.

* * * * *